United States Patent [19]

Tsuchiya

[11] Patent Number: 4,666,893

[45] Date of Patent: May 19, 1987

[54] METHODS OF INDUCING RESISTANCE TO BACTERIAL AND VIRAL INFECTIONS

[75] Inventor: Yoshiki Tsuchiya, Cincinnati, Ohio

[73] Assignee: St. Thomas Institute, Cincinnati, Ohio

[21] Appl. No.: 628,130

[22] Filed: Jul. 10, 1984

Related U.S. Application Data

[62] Division of Ser. No. 466,370, Feb. 15, 1983, abandoned.

[51] Int. Cl.$^4$ ............................................. A61K 31/685
[52] U.S. Cl. ....................................................... 514/78
[58] Field of Search ........................................... 514/78

[56] References Cited

U.S. PATENT DOCUMENTS

| | | | |
|---|---|---|---|
| 1,939,166 | 12/1933 | Hadjopoulos | 514/78 |
| 3,156,616 | 11/1964 | Mustard | 514/78 |
| 3,594,476 | 7/1971 | Merrill | 514/78 |
| 3,636,194 | 1/1972 | Parizeau | 514/78 |
| 3,752,886 | 8/1973 | Munder et al. | 514/78 |
| 4,263,286 | 4/1981 | Nakasima et al. | 514/78 |
| 4,369,182 | 1/1983 | Ghyczy et al. | 514/78 |

FOREIGN PATENT DOCUMENTS

| | | | |
|---|---|---|---|
| 58-135813 | 8/1983 | Japan | 514/78 |
| 2039738 | 8/1980 | United Kingdom | 514/78 |
| 2094623 | 9/1982 | United Kingdom | 514/78 |

OTHER PUBLICATIONS

*Current Therapy*, by Conn. MD, pp. 396–398 (1981).
Fauve, Chem. Abst. 85:10434p (1974).
Vediuina et al., Chem. Abst., 72:129617x (1968).
*Remington's Pharm. Sciences*, 16th Ed., pp. 393–396 (1980).

*Primary Examiner*—Albert T. Meyers
*Assistant Examiner*—F. Krosnick
*Attorney, Agent, or Firm*—Kinney & Schenk

[57] ABSTRACT

A variety of substances are known which promote host resistance to bacterial and viral infections, However, because of the unpredictable vagaries of such organisms, there is seemingly a never ending need for antimicrobials, particularly those with antiviral activity. Antimicrobials are provided herein which are effective in inducing resistance to infections due to such bacteria as staphylococci and such viruses as RS virus.

3 Claims, No Drawings

METHODS OF INDUCING RESISTANCE TO BACTERIAL AND VIRAL INFECTIONS

This is a division, of application Ser. No. 466,370, filed Feb. 15, 1983, now abandoned.

BACKGROUND OF THE INVENTION

This invention pertains to antimicrobials effective in protecting against bacterial and viral infections.

Although many antimicrobials have been suggested for the treatment of bacterial and viral infections, these diseases continue to be a problem. One reason for this is that bacteria such as staphylococcus, streptococcus, pseudomonas, etc., are a unique group of organisms which still present unanswered questions in biology, both fundamental and experimental. They are ubiquitous in distribution and have attained extreme degrees of diversification in biological and biochemical characteristics.

On a more specifice level, it is recognized that the significance of staphylococcal infections is not so much in severity, except in a few instances, as in the subtleties of the infections due to the unpredictable vagaries of these organisms. Treatment of staphylococcal diseases is complicated by the ability of the organisms to develop resistance to the drug being used in the treatment. Propionibacterium acnes on the other hand plays a role in the etiology of acne vulgaris by hydrolyzing sebaceous triglycerides, and by producing other factors that induce microcomedonal inflammation.

The magnitude of the problem of treating bacterial and viral infections is amplified by the extreme difficulty of total eradication and the frequent reappearance of the same strain even after apparently successful elimination. The inability to eliminate the carrier state by any of the currently known methods and the prevalence of the new antibiotic resistance hospital strains have added a new dimension to the frustrating situation.

The development of such multiple antibiotic resistant strains of bacterial organisms suggests the desirability of investigating additional means of combating bacterial infections. As a consequence, the development of drugs which are effective against microbials has attracted considerable attention. Staphylococcal and similar infections including chronic persistent and post surgical infections, have posed serious problems in the clinical field. As a consequence, there is seemingly a never ending demand for antimicrobial factors, particularly those with antiviral activities.

SUMMARY OF THE INVENTION

By means of this invention new antimicrobials are provided conferring remarkable resistance to bacterial infections. Moreover, their action appears to stimulate the immune system, most likely the cellular system. Consequently, the compositions herein are not only antibacterial but also antiviral. This invention is based on the discovery of antimicrobial activities of certain phospholipids. By the practice of this invention, it has been found that certain phosphatides are effective in inducing resistance to bacterial and viral infections.

DETAILED DESCRIPTION OF THE INVENTION

It has been accepted that staphylococcal virulence derives from the combined action of bacterial toxins and enzymes whose effectiveness is conditioned by the response of the host. As a consequence, phagocytic action against such microbials, as well as humoral action, has now been studied. We have found selected phospholipids to be related to the humoral immune system as well as to the cell mediated immune system. Unlike conventional antibiotics, the phospholipids of this invention may not necessarily be present in the blood stream of tissue in order to induce the activity. The reason for this is that the major activity of phospholipids is due to their immunogenic function. This function triggers the immune defense system. As a result, the phospholipids are effective antimicrobial, antiviral compositions.

Glycerophosphatides are esters of phosphatidyl glycerol. These esters are known compounds, generally isolated from tissues of animals, such as lungs, heart, liver, brain and the like. We have discovered that if at least one of the two acyl (ester) groups of the glycerophosphatide is unsaturated the glycerophospholipid demonstrates increased antimicrobial and antiviral activities. The major acids forming the glycerophosphatide ester groups are palmitic, stearic and oleic, the glycerophosphatides of the invention being phosphatidylserine, phosphatidylcholine, phosphatidylinositol and phosphatidylethanolamine. A desirable glycerophosphatide is beta-oleoyl-$\gamma$-palmitoyl-L-$\alpha$-phosphatidylcholine.

The protective action of the glycerophosphatide compounds of this invention against staphylococcal infection somehow resembles vaccines. However, the action of glycerophosphatides in connection with host immune system is quite different. As far as we know, vaccines do not have quick response (1 or 2 weeks responses), which is one of the keys to the importance of these new compounds. Vaccines are based on large molecular compounds such as proteins and usually multiple administrations of the preparation are necessary. Then, the expression of the activity begins three to four weeks after the first introduction and the activity is specific (limited to the type of antigens introduced). In contrast, phospholipids are not protein nor large molecular compounds present in our body. As far as we know, multiple administration of the compound is not essential. The earliest expression of the activity is 24 hours after administration and it may be shorter. The activity may last 3 to 4 weeks although the vaccine may last years or life time. The activity of glycerophosphatides is non-specific under the experimental conditions employed in our laboratory.

The high degree of resistance to stahylococcal infections obtained by administration of glycerophosphatides will best be apparent from their biological effects in in vivo studies using phosphatidylcholine (PC) as set forth in the following example and in the table accompanying the example.

Throughout the course of these studies Swiss albino mice, both male and female, were used. The animals were between 7 and 15 weeks old and had an approximate average weight of 20 to 25 grams. These animals were mostly raised and maintained on the Purina Lab Chow diet. The experimental animals obtained from the commercial animal farms or Kentucky farm were climatized at least one week in our laboratory prior to use for the study.

The assays were conducted using a penicillin-resistant strain, *Staphylococcus aureus* Original, first isolated from a case of acute tonsilitis and maintained in our laboratories for years. This strain is preserved in the lyophilized form and stored at 0° C. to 8° C. and stock cultures were grown on blood agar. A culture from the mother culture was used for preparing a blood bacterial suspension for challenge. For testing, the inoculum was prepared as 18-24 hour cultures from blood agar (sheep, human or rabbit). The cells were washed and suspended in physiological saline (0.9% sodium chloride solution). Following conventional procedures, a dose killing 50 to 70 percent ($LD_{50-70}$) was used in these investigations. The $LD_{50-70}$ was determined by intraperitoneal infection noting the mortality over a 5-day period.

EXAMPLE A

Single doses of 50 mg semi-purified PC dissolved in 0.5 ml of 0.9% saline solution were injected intraperitoneally (in separate tests) at time intervals ranging from one week prior to challenge to administration immediately after challenge with $3 \times 10^8$ S. aureus organisms.

Commercial crude bovine lecithin was dissolved in petroleum ether. After separating the petroleum ether-soluble fraction, five volumes of acetone were added producing a precipitate. The precipitate was then treated with absolute ethanol. The absolute ethanol-soluble material was dried under vacuum, follwed by treatment with 12% trichloroacetic acid. The petroleum ether and acetone purification steps were repeated. The final product was dried under vacuum and tan granules were obtained.

TABLE A

| | Phosphatidylcholine Protection Against S. aureus Infections in Mice | | | | | | |
|---|---|---|---|---|---|---|---|
| Time PC* | Control | | | Experimental | | | |
| Prior to Challege | No. of Mice | No. Dead 5 Days | % Mortality | No. of Mice | No. Dead 5 days | % Mortality | % Protection |
| 24 hours | 154 | 87 | 56.5 | 145 | 16 | 10.4 | 81.0 ± 13.0 |
| 48 hours | 148 | 85 | 57.4 | 146 | 12 | 8.2 | 82.7 ± 7.2 |
| 72 hours | 18 | 10 | 55.5 | 35 | 4 | 11.1 | 81.2 ± 4.1 |
| 1 week | 101 | 66 | 65.3 | 127 | 14 | 11.0 | 83.2 ± 3.6 |

*Phosphatidylcholine. +Mean ± Standard Deviation.

The results given in table A show that when the experimental mice are given a single injection of PC at times ranging from 24 hours to 7 days before challenge with S. aureus, 78 to 85% were protected as compared to the untreated control mice. Additional data obtained in the same manner show that the PC was effective when given 4 weeks, 3 weeks, and 2 weeks prior to the staphylococcal infection. Recent studies on minumum effective dosage show that microgram doses of further purified bovine lecithin give better protection against the staphylococcal infection than the previous 50 mg dose studies.

We will now show the effectiveness of our material in the treatment of viral infections.

EXAMPLE B

Infectivity of respiratory syncytial virus (RSV) was assayed by the plague-reduction method. Hep-2 cells were grown to 85-90% confluency. Group 1 received 250 ug/ml PC in standard medium 24 hours before viral infection. Group 2 received the same pretreatment with PBL but also received a second treatment with 250 ug/ml of PC after infection. Group 3 was treated with PC only after infection. Control Group 4 was untreated. In all groups after 24 hours, cell monolayers were washed and infected with RSV. The plates were incubated until the cell monolayers were completely destroyed. The supernatants of each group were pooled and titered on Hep-2 cells for plague-forming virus. Group 1 showed a 50% reduction in plague-forming units (pfu/ml) as compared with the control. Group 2 showed a 97% reduction in pfu/ml, while Group 3 showed a 85% reduction. Thus, PC was effective when added to Hep-2 cells either before or after infection. Assays of the bacterial population in the livers of control and experimental mice show a very large decrease in the number of bacteria in the animals treated with PC, compared to the control mice.

Example B thus shows that syncytial virus infections are markedly reduced by treatment with PC. It will now be shown that, PC also brings about a reduction of inflammation reactions induced by intradermal injection of Propionibacterium acnes.

We have found that intradermal injection of P. acnes in the shaved backs of rabbits produces erythema and nonpustulating inflammatory nodules that persist more than 8 weeks. These findings suggested that injection of a mixture of PC and P. acnes might produce enhanced inflammatory reactions in rabbits, possibly because PC might act as a hydrolyzable artificial sebum in these animals which lack sebaceous glands. On the contrary, we have found that PC has an anti-inflammatory activity which reduced the reaction of rabbits to intradermal injection of P. acnes. This will be apparent from the following example.

EXAMPLE C

Randomly bred rabbits were prepared as reported in the Journal of Investigation in Dermatology (1981) Vol. 76 at p. 314. A 2% PC solution, i.e., 2 g of bovine PC, purified by methods described earlier (1), were suspended in 100 ml of thioglycollate medium without added dextrose (BBL Microbiological System, Cockeysville, MD). Three different concentrations of P. acnes, strain #6919 obtained from Anerican Type Culture Collection, Rockville, MD, were prepared by growing the bacteria in a thioglycollate medium for 48 h. The bacteria were harvested, washed twice and resuspended in normal saline to contain $10^5$, $10^6$, $10^7$ cells. Prior to intradermal injections at 4-7 sites on the shaved backs of rabbits, bacteria were mixed with PC. Animals were divided into 3 groups. The first group (control) was injected with saline or sterile medium. The second group received P. acnes alone, and the third received P. acnes mixed with PC. The two latter groups were subdivided to receive single doses of 0.05 ml of each bacterial concentration. Care was taken to keep the PC and the medium in which it was suspended in reduced form. The oxidized form turned blue-green because of the indicator incorporated in the medium (methylene blue). All animals were kept for observation for an 8-week period. Nodules and erythema were measured and compared. At days 1, 5, 15, and after 8 weeks, nodules were excised from each group, immediately fixed in 10% buffered formalin, histologically prepared by routine histopathological methods and stained with hematoxylin and eosin. The results of the these observations are given in Table C.

TABLE C

|  | Control injected with saline or medium | Exptl injected with P. acnes alone | Exptl injected with P. acnes in PC |
|---|---|---|---|
| No. of animals | 20 | 38 | 42 |
| No. of P. acnes injected | 0 | $10^5, 10^6, 10^7$ | same |
| Appearance time in hr[b]: |  |  |  |
| erythema | $0^c$ | $5 \pm 2$ | $21 \pm 4$ p = 0.01 |
| nodules | 0 | $16 \pm 3$ | $25 \pm 4$ p = 0.10 |
| Sizes in mm: |  |  |  |
| erythema | 0 | $13 \pm 3$ | $7 \pm 2$ p = 0.025 |
| nodules | 0 | $8 \pm 1.5$ | $5 \pm 2$ p = 0.50 |
| Time of resolution of nodules in wks | immediate[c] | $8 \pm 1$ | $4 \pm 2.5$ p = 0.05 |

[a]Comparison between the groups of rabbits injected with P. acnes alone or suspended in PC before injection was done using Student t-test (2-tailed).
[b]Since the vesicles which erupted at the site of injection with saline or PC suspension subsided within 1 hr, the time of appearance reflects and is included in this calculation.
[c]Because the eruption of vesicles subsided in all animals or within 1 hr, this time in control is baseline, or zero.

All of the animals showed dermal neutrophilic inflitration and edema between days 1 and 5. There was a shift of leukocytic inflitration from all neutrophila to mononuclear phagocytes at day 15 until the end of the experiment. Also observed was moderate to severe hyperkeratosis, most prominent in the group which received P. acnes. There was a remarkable delay in appearance of erythema and nodules, a reduction in sizes of erythema and nodules, and the time of resolution of the nodules was significantly shorter in the animals receiving PC. We suggest that the reduction by PC of inflammoatory reactions induced by intradermal injection of P. acnes in rabbits may be an interaction between the PC with the cell-mediated response of the animals in inhibiting the proliferation and spread of bacteria, thus preventing the bacteria from producing the inflammatory mediators. Even if the bacteria escape to release the microbial products responsible for inflammation, it is likely that there will be a competition between the PC molecules and microbial products (enzymes, etc.) for adsorption to the target cells.

Because of the immediate protection evident at 24 hours, together with the additional findings mentioned above, it seems plausible to say that the cell-mediated response may be responsible, at least in part, for the prophylactic effect shown by PC. The effect was evident in each case. Similar results are obtained with other glycerophosphatides having an unsaturated acyl group.

The compositions of this invention thus constitute a significant new class of anti-infectious agents. Where exposure to staphylococci, streptococci or viral infections are likely, the drug will be prescribed. In conventional antibiotics where there is a direct interaction between the drug and the invader, heavy doses of the drug are required. As indicated, treatment herein requires only sufficient phospholipids to trigger the immune defense system. The preparation will be administered by intramuscular, intraperitoneal, or intravenous injection of preferably 0.1 to 5 mg doses. The activity will remain at least 2 to 3 weeks after injection. To prepare the drug, a proper concentration of the phospholipid, preferably 5 mg/ml may be made in saline or other media and stored in a refrigerator. Other antiseptic agents such as merthiolate can be included if desired. Thus, a process is provided for the control of viral and bacterial infections in humans and other mammals which involves administering to the mammal in need of the drug an effective amount of glycerophosphatide. Various diluents, doses, and other variations and modifications will occur to those skilled in the art. Thus, oral administration can be achieved by using time-release capsules which dissolve in the intestine, preventing degradation, hydrolysis or oxidation of the phospholipid in the stomach. Tablets or time-release micro capsules may be used. Such ramifications are deemed to be within the scope of this invention.

What is claimed is:

1. A method of treating respiratory syncytial virus infections in mammals comprising administering to a mammal in need of said treatment an effective amount of a glycerophosphatide selected from the group consisting of phosphatidylserine, phosphatidylcholine, phosphatidylinositol and phosphatidylethanolamine isolated from tissues of animals, and having at least one unsaturated acyl group.

2. The method of claim 1 whreein the acyl groups are linoleoyl and myristoyl groups.

3. The method of claim 1 whrein the acyl groups are oleoyl and palmitoyl groups.

* * * * *